United States Patent
Gluckman et al.

(10) Patent No.: US 8,718,755 B2
(45) Date of Patent: May 6, 2014

(54) METHODS AND DEVICES FOR DETERMINING BRAIN STATE

(75) Inventors: Bruce Gluckman, Arlington, VA (US); Kristen Richardson, Fairfax, VA (US); Steven Weinstein, Washington, DC (US); Steven Schiff, Chevy Chase, MD (US)

(73) Assignee: George Mason Intellectual Properties, Inc., Fairfax, VA (US)

( * ) Notice: Subject to any disclaimer, the term of this patent is extended or adjusted under 35 U.S.C. 154(b) by 1078 days.

(21) Appl. No.: 10/533,421

(22) PCT Filed: Nov. 3, 2003

(86) PCT No.: PCT/US03/34789
§ 371 (c)(1),
(2), (4) Date: Jul. 23, 2007

(87) PCT Pub. No.: WO2004/041069
PCT Pub. Date: May 21, 2004

(65) Prior Publication Data
US 2008/0045853 A1 Feb. 21, 2008

Related U.S. Application Data

(60) Provisional application No. 60/422,870, filed on Nov. 1, 2002.

(51) Int. Cl.
*A61N 1/00* (2006.01)

(52) U.S. Cl.
USPC ........ 607/2; 607/1; 607/44; 607/45; 600/377; 600/378; 600/544; 600/545; 600/554

(58) Field of Classification Search
USPC ........ 600/377–378, 544–545, 554; 607/2, 44, 607/45, 1
See application file for complete search history.

(56) References Cited

U.S. PATENT DOCUMENTS

| | | | |
|---|---|---|---|
| 6,363,279 B1 | 3/2002 | Ben-Haim et al. | |
| 6,665,562 B2 * | 12/2003 | Gluckman et al. | 607/2 |
| 6,671,555 B2 * | 12/2003 | Gielen et al. | 607/45 |
| 6,690,974 B2 * | 2/2004 | Archer et al. | 607/45 |

\* cited by examiner

*Primary Examiner* — Michael Kahelin
*Assistant Examiner* — Mallika D Fairchild
(74) *Attorney, Agent, or Firm* — Sagun KC (57) ABSTRACT

The present invention relates to methods and devices for determining the state of a neural system. In one embodiment, a plurality of stimuli to the system can be delivered to the system, and then the resulting respective responses can be analyzed to determine whether the system state is static, or whether it is undergoing dynamic changes. In another aspect of the invention, a single stimulus having a plurality of components can be administered, and the responses to each component can be contrasted and compared to determine the state of the neural system. In each case, this information can be used to predict the occurrence of neural perturbations or episodes associated with a change in the state of the neural system.

23 Claims, 7 Drawing Sheets

METHODS AND DEVICES FOR DETERMINING BRAIN STATE

This application claims the benefit of U.S. Provisional Application Ser. No. 60/422,870, filed, Nov. 1, 2002, which is hereby incorporated by reference in its entirety.

STATEMENT AS TO RIGHTS TO INVENTIONS MADE UNDER FEDERALLY SPONSORED RESEARCH AND DEVELOPMENT

The U.S. Government may have certain rights in these inventions pursuant to grant number R01 MH01493 awarded by National Institute of Health.

BACKGROUND OF THE INVENTION

Neural systems are dynamically changing ensembles of neurons and other associated cells that continuously respond to stimuli and other endogenous and exogenous input. These systems produce complex behaviors that involve the propagation of electrical activities within the neuronal ensemble. While much of this behavior is normal and has practical value to the system, occasionally neural activity occurs which perturbs the system in injurious and/or undesirable ways. An example of such a behavior is epilepsy, a disease characterized by unpredictable electrical discharges in the brain. Not only can a seizure damage the brain, but when it causes a loss of consciousness, the patient can be injured in a fall. The ability to predict the occurrence of a seizure, and other perturbations to a neural system, is therefore important to avert injury.

DESCRIPTION OF THE INVENTION

The present invention relates to methods and devices for determining the state of a neural system. By the term "state," it is meant the condition of the neural system as characterized by any measurable quality or attribute of it. For instance, when the neural system is a brain, its condition can be described by its ongoing electrical activity, e.g., as measured extracellularly using a suitable recording device.

In accordance with the present invention, the state of the neural system can be assessed by analyzing its response to a delivered stimulus or other perturbation. A change in the state of the neural system will be reflected by the system's response to the stimulus. In one embodiment, a plurality of stimuli to the system can be delivered to the system, and then the resulting respective responses can be analyzed to determine whether the system state is static, or whether it is undergoing dynamic changes. In another aspect of the invention, a single stimulus having a plurality of components can be administered, and the responses to each component can be contrasted and compared to determine the state of the neural system. By continuously and simultaneously stimulating and recording activity in the system, information can be gathered which is useful in predicting the occurrence of neural perturbations, e.g., associated with epilepsy (e.g., seizures), motor disorders, vocal tic disorders, Tourette's Disorder, depression, anxiety disorders, etc. It can also be used to assess the state of sensory cortex (visual, somatosensory, and auditory, etc.), motor cortex, spinal cord, etc.

Along these lines, the present invention relates to methods and devices for detecting a preseizure and/or predicting an impending seizure in a neural system by analyzing the system's response to a stimulus or perturbation. For example, the present invention relates to methods and devices for detecting an impending seizure and/or preseizure in a neural system, comprising one or more of the following steps in any effective order, e.g., applying a stimulus to a neural system, detecting the response of the neural system to the stimulus, and determining whether the response is different from a response during the interictal state. The terms "preseizure" and "impending seizure" are used interchangeably to indicate the neural state that precedes the characteristic neural activity described as a "seizure."

The present invention also relates to methods and devices for detecting an impending seizure and/or preseizure in a neural system, comprising one or more of the following steps in any effective order, e.g., applying a stimulus, comprising a multitude of phases which may include positive, negative, and zero phases, to a neural system, detecting the response of the neural system to the stimulus, and determining whether the response is indicative of a change in state. State changes may be determined using classification schemes based upon measured data and a system model. The system model may include multivitiate statistical discrimination. The multivariables may include sub-responses during the various phases of the various stimulations.

A neural system in accordance with the present invention can be any ensemble of one or more neurons, and/or other excitable cells, such as muscle, heart, retinal, cochlear, tissue culture cells, stem or progenitor cells, including cell-electrode interface devices and the like. Cells can be coupled electrically, chemically, or combinations thereof. The neural system can be an entire brain, spinal cord, ganglia, nerve, etc., or it can be a region or portion of it. Any animal source of material is suitable, including neural systems of invertebrates, such as mollusks, arthropods, insects, etc., vertebrates, such as mammals, humans, non-human mammals, great apes, monkeys, chimpanzees, dogs, cats, rats, mice, etc. Preferred target regions or brain structures include, but are not limited to, neocortex, sensory cortex, motor cortex, frontal lobe, parietal lobe, occipital lobe, temporal lobe, thalamus, hypothalamus, limbic system, amygdala, septum, hippocampus, fornix, cerebellum, brain stem, medulla, pons, basal ganglia, globus pallidum, striatum, spinal cord, ganglion, cranial nerves, peripheral nerves, retina, cochlea, etc.

A stimulus can be applied to a neural system in order to elicit a response from it. The term "applied" indicates that the stimulus is administered or delivered to the system in such a way that it reacts to it with a measurable response. The stimulus can be applied directly to the same loci where the response is measured, or it can be applied remotely at a distance from it. For instance, the stimulus can be applied on one side of a neural system (e.g., a brain), and then the response to it measured contralaterally.

The stimulus can be of any kind, e.g., electrical, magnetic, pressure, or other force, that produces a characteristic response upon perturbation of the neural system, e.g., a brain, or structure thereof, in a preseizure state or when a seizure is impending. It can comprise one or more components. For example, a stimulus can be an electrical stimulus presented in any effective form, e.g., as an electrical field, electrical potential difference, electric current, etc. The electrical stimulus can be of any amount or charge that is effective for probing and eliciting information about the state of the neural system. In the examples below, a subthreshold full-wave electrical stimulus having both positive (excitatory), negative (suppressive), and zero (baseline) phase components was administered to a neural system. When an excitatory response not normally observed during the interictal state was detected, this was followed by a full-blown seizure episode, indicating that it was a signal or sign of an imminent seizure.

Stimuli in accordance with the present invention are minimally intrusive on the electrical activity, neural processing, behavior, and other characteristics of the neural system. Such stimuli can facilitate subtle probing of ongoing activity with minimal impact on the neurons, while conferring the ability to simultaneously record from the system for extensive periods of time. Moreover, these stimuli minimize potential damage to the neural system. Utilizing low frequency and/or low energy content stimuli permit the state of the neural system to be assessed in ways that do not significantly perturb the normal functioning and behavior of the neural system as a whole.

As explained in more detail below, these stimuli can have one of more of the following characteristics or properties, but not limited to: subthreshold, consisting of or comprising low frequency content, continuous waveform, arbitrary waveform, and/or where the electrical stimulus comprises an arbitrary waveform that is determined adaptively by the magnitude and frequency of a preceding or concurrent response.

A subthreshold electrical stimulus is an electrical stimulus which is inadequate or insufficient to reliably produce action potentials in the neurons which occupy the region across which it is applied. A subthreshold electrical stimulus to the neural system, however, can cause measurable changes in the system's activity. This modification of the activity is a result of the modulation of the neuron firing rate produced by electrical (neuronal) inputs that are endogenous to the system. In mechanistic terms, without being bound by any theory, the firing rate of the neurons which comprise the neural system are determined by a neuron's firing threshold and the excitatory/inhibitory inputs to it. A subthreshold and exogenous stimulus does not by itself initiate neuron firing (action potentials), but instead modifies the neuron's sensitivity to its normal inputs (e.g., by changing the electrical threshold to reliably produce an action potential). As a consequence, the local field potentials, or other measure of the system's activity, can be affected by the administered stimulus.

A stimulus may be characterized as being subthreshold depending upon the specific characteristics of the neurons (e.g., number and type of inputs, resting membrane potential, ion channel type and quantity, etc.), the architecture and composition of the neural system, the nature of the applied stimulus, how it is administered to the neural system, etc. For example, the strength (e.g., applied current or voltage), duration, and frequencies of the stimulus can be selected such that they are not adequate to produce a threshold change across the cell membrane effective in initiating one or more action potentials. In such a case, a time-scale (e.g., in hertz or msec) and amplitude (e.g., in current or volts) is utilized which does not directly produce action potentials in the neurons affected by it. The subthreshold and continuous stimuli administered in the examples satisfy these conditions. Although a modulatory effect was observed, it did not reliably produce excitatory discharges in the neurons that comprised the neural system.

A subthreshold potential is, for example, less than 100 mV/mm, preferably 50 mV/mm and less, more preferably, 25 mV/mm and less, such as 20 mV/mm, 15 mV/mm, or 10 mV/mm. The subthreshold potential refers to the potential generated at the level of the target neurons. The amount of potential actually produced by the field electrodes is less important that the field perceived by the target neurons. It is the generated field sensed by the neurons that determines whether a stimulus is sub- or supra-threshold.

A stimulus can also be defined by its frequency content. A useful stimulus in accordance with the present invention can comprise or consist of low frequency content. The latter can be defined functionally, where "low frequency content" indicates that the frequencies of the waveforms that comprise the stimulus are less than the typical firing rate (e.g., action potentials per second) of the neurons in the targeted region. Such a stimulus can comprise any suitable and effective low frequency range, e.g., from about less than or equal to 100 Hz. Low frequency stimuli can be delivered by any suitable devices and electronics, e.g., as described by Gluckman and Schiff in US 2003/0114886. The low frequency stimuli utilized in the present invention can also be characterized as low in comparison to traditional pulse stimulation as described in US 2003/0181955, whose mode of stimulation can optionally be specifically excluded from the present invention.

As illustrated in the examples, a continuous stimulus can also be applied to the neural system. This indicates that the waveform which is injected into the system is applied without interruption. A particular continuous stimulus can be comprised of one or more periods or cycles having low frequency content. For example the frequency content may less than 100 Hz, and/or in a range, e.g., from about 0.1-100, 1-10, 0.1-10 Hz, etc., or any value or range in between. As indicated elsewhere, where the stimulus is comprised of a plurality of cycles, each cycle does not have to have the same form, but can differ in successive cycles, where the stimulus as a whole is aperiodic.

A stimulus that is utilized in the methods of the present invention can thus be a single, time continuous perturbation. This is in contrast to Lopes da Silva et al., *Prog. Brain Res.,* 102:359-370, 1994, and US 2003/0181955, each who described a time separated (pulsatile) pair of discrete suprathreshold high frequency content stimuli. Such mode of stimulation can optionally be excluded from the present invention.

In another aspect of the present invention, an electrical stimulus can be applied which comprises an arbitrary waveform that is determined adaptively by the magnitude and frequency of a preceding and/or concurrent response. Neural systems can be dynamic, and the underlying neurons may receive a continuously changing array of inputs. Consequently, a stimulus at one given time that is suitable for probing the neural system state (e.g., where the stimulus is subthreshold or comprises particular low frequency content), may at another time be unsuitable as a probe (e.g., where the stimulus evokes a volley of action potentials which interferes with the normal activity of the system). To account for this, a feedback system can be utilized to continuously adjust the duration, frequency, strength, etc. of the stimulus, e.g., to ensure that it does not result in suprathreshold stimuli or stimuli that evoke excessive perturbations to the system. The latter can also be referred to as "adaptive." Such a stimulus can therefore be arbitrary or aperiodic, where the waveform is continually adjusted as the response to it changes.

Any suitable waveform can be utilized. Waveforms can be periodic, aperiodic, sinusoidal, arbitrary, dynamically calculated, etc. Aperiodic or arbitrary shaped waveform can also be used, e.g., to avoid entraining the neural system, and also when a response is used to adaptively determine successive stimuli.

As discussed above, the method in accordance with the present invention involves applying an electric stimulus to the neural system effective to evoke an informational response, i.e., a response that can be used to assess the neural state. The electrical stimulus can be characterized by any suitable measure, e.g., current, voltage, field strength, etc.

An applied electrical stimulus, e.g., an electrical current or voltage, can be oriented in a particular direction with respect to the somatic-dendritic axis of the neurons in the neural system. For instance, an electrical field can be generated which is parallel to the somatic-dendritic axis.

In certain embodiments of the present invention, two pairs of electrodes can be used in the field application step. A pair of "field electrodes" can be used to produce the applied field. A second pair of electrodes, "sensing electrodes," can be used to measure or sense the field generated by the "field electrodes." The sensing and field electrodes can comprise the same materials described for the measuring electrodes. In certain applications, however, such as in vivo applications, a field can be applied without sensing electrodes.

Any effective electrodes can be used for the recording, sensing, and field electrodes, including, e.g., metal, steel, activated iridium, tungsten, platinum, platinum-iridium, iridium oxide, titanium nitride, silver chloride, gold chloride, etc., where the electrode can be insulated by glass or lacquer (includes both macroelectrodes and microwires), as well as silicon microelectronics, including tetrode or other multielectrode arrays or bundles, multichannel and ribbon devices. Typically, the electrodes can have relatively large tips with low resistance to detect activity from a number of neuronal elements within the neural system. Smaller tipped electrodes can be used for monitoring activity from single neurons or smaller populations. Activity can be measured from one or more electrodes, preferably two or more. In some cases, it may be desired to record from several regions of the neural system in order to characterize its activity. Recordings of intracellular, extracellular, or a combination thereof, can be analyzed separately, or together. The preamplifier can be AC- or DC-coupled.

For certain purposes, electrically reversible, such as iridium oxide type electrodes, may be preferred since they are relatively nontoxic to cells, as well as being effective carriers of high current and charge densities. An activated iridium or iridium alloy wire can be used, or a metal substrate, such as noble metal (e.g., Au, Pt, or PtIr), ferrous steel alloy, stainless steel, tungsten, titanium, Si microprobe, etc., or other suitable substrate, can be coated with a film of iridium oxide to produce an effective electrode. Any suitable method to prepare the coating can be used, including, but not limited to, an activation process (e.g., Loeb et al., *J. Neuro. Sci. Methods,* 63:175-183, 1995; Anderson et al., *IEEE Trans. Biomed. Eng.,* 36:693-704, 1989) to form activated iridium oxide films (AIROFs), thermal decomposition (Robblea et al., *Mat. Res. Soc. Symp. Proc.,* 55:303-310, 1986) to form thermal iridium oxide films (TIROFs), reactive sputtering (15) to form sputtered iridium oxide films (SIROFs), electrodepositing (Kreider et al., *Sensors and Actuators,* B28:167-172, 1995) to form electrodeposited iridium oxide films (EIROFs), etc.

The electrodes can be positioned in any arrangement which is effective to produce a suitable stimulus. The electrodes for stimulation can be in contact with brain tissue or associated meninges, e.g., by inserting, through an occipital entrance hole, one, or more, long flat electrode strips that contacts the long axis of the hippocampus surface in the temporal horn of the lateral ventricle. A round electrode (e.g., an electrode array such as a single depth electrode with one or more suitable high current contacts) can also be utilized, e.g., by placing it within the long axis of the hippocampus in order to produce a radial electric field. Electrodes can also be external to the brain, e.g., subdural, epidural, or on the scalp. The electrode strip preferably produces a subthreshold electric field. Useful electrode strips include non-polarizing biocompatible electrodes embedded in silastic sheets with sealed electrode-lead connections, similar to those used for cochlear implants, e.g., a Clarion Cochlear Implant, comprising iridium oxide electrodes sealed within a curved silastic silicone elastomer sheath. In another embodiment, a sheet comprising multiple electrodes can be placed over the neocortex in the subdural, subarachnoid, or epidural spaces, or within the sulci of the brain. Thin electrodes can also be inserted into brain tissue. In general, any types or combinations of electrodes, such as those mentioned above, can be used.

For example, for use with a subject with focal hippocampal epilepsy, one could implant a pair of axial electrode arrays along the axis of each hippocampus. An electrode array may include a multitude of contacts. Then, through passive recording, the seizure focus may be determined. Some of the electrode surfaces may be selected for stimulation purposes. Finally, at least some of the electrodes not being used for stimulation purposes may be used for measurement and characterization purposes.

The response to the stimuli which is used as the descriptor of the neural state can be any measurable phenotype or physiological output of the system. This includes, but is not limited to, e.g., neuronal activity (see below), electrical, chemical, or magnetic activity, heart rate, pupil dilation, eye movement, body temperature, muscle tone. Generally, any detectable or measurable response to a stimulus can be used in the present invention to determine neural system state.

The neuronal activity of the neural system can be measured to determine whether the stimulus provokes a response that is different from a response elicited when the brain is in a different state. For example, where epilepsy is the disorder, the neural activity can be probed with a stimulus to determine when the brain shifts from its "normal" interictal state (i.e., the period between seizures), to a state indicative of an impending seizure.

By the term "neuronal activity," it is meant any measurable physical behavior, output, or phenotype of the system. For example, neurons typically display variations in their membrane potential, such as action potentials, depolarizations, and hyperpolarizations. These changes in the membrane potential can be utilized as a measure of neuronal activity, e.g., by monitoring intracellularly in a single neuron, or extracellularly, the electrical activity of a single neuron or the activity of an ensemble of neurons. Behaviors, or other products of a neural system (e.g., hormones, growth factors, neurotransmitters, ions, etc.) can also be detected, and used determine the brain state.

The neuronal activity which is measured or assessed can be the complete neuronal activity exhibited by the system, or a subset of the total activity, e.g., a particular frequency band of the full neural signal. The measuring electrodes can detect various types of activity, e.g., spontaneous neuronal firing, slow burst activity, and background noise.

Methods for measuring and recording neuronal activity can be accomplished according to any suitable method. In certain embodiments of the invention, the neuronal activity is monitored extracellularly by measuring the extracellular electrical potential of a target population of neurons. Such measurements can reveal complex spikes or burst activity, sharp or slow waves, epileptiform spikes or seizures, arising from one or more neurons in the neural system.

The neuronal activity can be measured by recording the neural system's electrical potential in the extracellular space. The electrodes used to measure the field potential produced by the neural system are referred to as "measuring electrodes" or "recording electrodes." One or more electrodes can be used to measure the field potential. In preferred embodiments, two or more electrodes are utilized. The field potentials recorded at a given extracellular site will depend on a variety of factors, including the location of the electrode(s) with respect to the soma and dendritic layers, the architecture of the neural system, the perfusion solution, etc.

The measuring electrodes can detect the field potential from the applied field as well as the activity generated by the neural system. There are a number of methods that can be used to distinguish the neuronal activity from the applied fields. For example, in in vitro hippocampal slices, a pair of differential electrodes, aligned as closely as possible to the isopotential of the applied field, were used as measuring electrodes. They are "differential" in the sense that an active electrode is placed in the tissue, preferably near the cell body layer of the target neurons, while the reference electrode is placed preferably in the bath external to the tissue. The values obtained from each electrode can be electronically subtracted from each other, reducing background noise. For in vivo use, the differential measuring electrodes can be placed at the same isopotential with respect to the applied field. The electrodes can be as close to the target population as possible, without damaging it. Other methods to reduce noise and the artifact from the applied field can be used as well, either alone, or in combination with the differential electrodes, including filtering and post-processing of the measured signal.

The signal recorded from the system can be processed to dissociate the applied field potential from the electrical activity expressed by the neurons. As mentioned above, placing the electrodes on an isopotential is one way to remove the applied field potential from the recorded signal. However, constraints imposed by the geometry and accessibility of the neural system may make placement of the electrodes along the isopotential impractical. In those cases, signal processing can be utilized. In simple terms, the goal of signal processing is to cancel any electrical field potential component, and associated noise, generated by the applied field input, so that the measured output can be attributed substantially to the activity of the neurons. Any processing method or technology which accomplishes this task can be used. The invention is not limited to how the processing is actually implemented, or the approach that is used.

The field potential contributed by the applied field can be determined using a relatively simple method. It is well-established that the potential difference between two points in a resistive medium generated by an applied field is proportional to the applied current used to generate the field. The proportionality constant will depend upon the specific properties of the system, e.g., its geometry, the conductive characteristics of the cells and tissues, the amount of fluid present, etc. Once the proportionality constant is known, the amount of potential produced by the field can be calculated, and then subtracted from the recorded signal. The proportionality constant can be determined mathematically from computer models accounting for the properties of the neural system, or it can be derived empirically. To make an empirical determination, a test signal can be inputted into the system, and then the resulting output can be measured. These two values (i.e., test signal and associated output) can be used to determine the constant. The derived proportionality constant can be used in the form of an algorithm to process the recorded signal. The algorithm can be implemented in any suitable hardware or software form.

Recording from the electrodes can be performed routinely. For instance, measurements can be made with an AC amplifier if the frequency and number of extracellular bursts are of interest. It can be equipped with filters to cut off frequencies below and above a particular range (band-pass filter) and amplify the signal in preferred ranges, e.g., 50-1000 Hz, preferably, 100-500 Hz. A DC amplifier can also be used, if slower potential changes are of interest.

The measured neuronal activity can be characterized by any suitable method that enables it to be used to determine the state of the neural system. Neuronal activity can be characterized by various measurements, depending upon the particular activity that is being assessed. When electrical activity is a determinant, then measurements can include, e.g., local field polarity and magnitude (e.g., $-10$ mV), burst activity, burst amplitude, burst frequency, power in a predetermined frequency band of activity, non-burst activity, single or small population firing rate, amplitude or phase of periodic activity, such as theta rhythm, root-mean-square (RMS), variance, etc.

The measurements may then be characterized using any number of techniques. For example, frequency spectral information may be extracted using processing techniques such Fast Fourier Transforms (FET), convolution through wavelets, filter bank processing, discrete cosine transformation methods, or other signal processing methods known to extract frequency spectral information. This frequency spectral information may then be further analyzed by looking at distinguishing aspects such as frequency time variations, mean frequency content, and ratio's of frequency power.

Once a response to a stimulus is elicited and measured, it can be compared to other responses in order to determine the neural system state. Comparisons can be between responses elicited on the same day, the same sequential time period, etc., between average or standard responses stored in a database, or between phases of the same response. For example, responses can be sequentially collected, and then continuously compared to each other to determine when enough statistical variance has occurred to indicate a change in the neural system state. Any sampling procedure can be used to derive response measurements useful in determining changes in neural system state.

In addition to comparing responses elicited by separated stimuli, a response to a single stimulus can be dissociated into components, and then these components can be compared and contrasted within the same response. For instance, a full-wave stimulus comprises at least four phases: positive, positive-zero (when the wave passes from positive to zero), negative, and negative-zero (when the wave passes from negative to zero). When a sinusoidal wave is applied, the resulting response to a single cycle can be dissociated into its positive, zero, and negative phases. The response associated with each phase can be compared against each other in order to obtain a description of the neural system state, and compared to corresponding phases of different responses.

Any device which is suitable for delivering a stimulus to a neural system can be utilized in accordance with the present invention. Suitable devices include, e.g., those described in Gluckman et al., J. Neurosci., 21:590-600, 2001 and 20030114886.

The excitatory response, or any other signal detected after an appropriate stimulus is delivered to a neural system, can be used in accordance with the present invention to detect and warn of an impending seizure. Moreover, once the signal alerts that a seizure is imminent, appropriate measures can be taken to intervene in the seizure episode, e.g., by treating and/or suppressing it, by taking precautionary measures so that the subject is not injured during it, by injecting an appropriate agent that will inhibit or suppress the seizure, etc.

Adaptive electric field modulation of neural systems can be performed as described in US 20030114886 (Gluckman and Schiff). For example, as described therein, the method involves applying an oriented electric field to said neural system effective to suppress the seizure activity of the neural system, wherein the magnitude and polarity of said oriented electric field is changed in response to the measured neuronal activity, and the measuring of neuronal activity is performed simultaneously and continuously with the applied field.

EXAMPLES

Materials and Electronics

Surgical Procedures.

Male Sprague-Dawley rats (e.g., average 284 g; 65 days old) may be anaesthetized with a Ketamine/Xylazine (KX) mixture of 100 mg/ml Ketamine with 20 mg/ml Xylazine in a ratio of 8:1 by volume, administered in doses of 0.1 ml/100 g. Once the animal becomes areflexive, which may be determined by toe or tail pinch, ear and incisor bars may be used to stabilize the animal. To maintain areflexia, additional doses of KX may be administered throughout the experiment. Core temperature may be monitored with a rectal thermometer and controlled with a heating pad. To expose the skull, a vertical incision may be made from the anterior frontal bone to the external occipital crest. Next, a 4 mm wide craniotomy may be performed bilaterally from the coronal to the lambdoid sutures leaving a 2 mm strip of bone over the sagittal sinus intact. Opening the dura mater that covers the left hemisphere may expose the neocortex. To enter the body of the lateral ventricle and expose the dorsal surface of the hippocampus, a left neocortical window may be created with aspiration. On the right, a small opening may be created in the center of the dura for stereotactic electrode insertion. Both exposed brain areas may be kept moist with a layer of artificial cerebrospinal fluid (ASCF) containing (in mM): 155 $Na^+$, 136 $Cl^-$, 3.5 $K^+$, 1.2 $Ca^{2+}$, 1.2 $Mg^{2+}$, 1.25 $PO_4^{2-}$, 24 $HCO_3^-$, 1.2 $SO_4^{2-}$ and 10 dextrose.

Recording Electronics.

Figure 1:
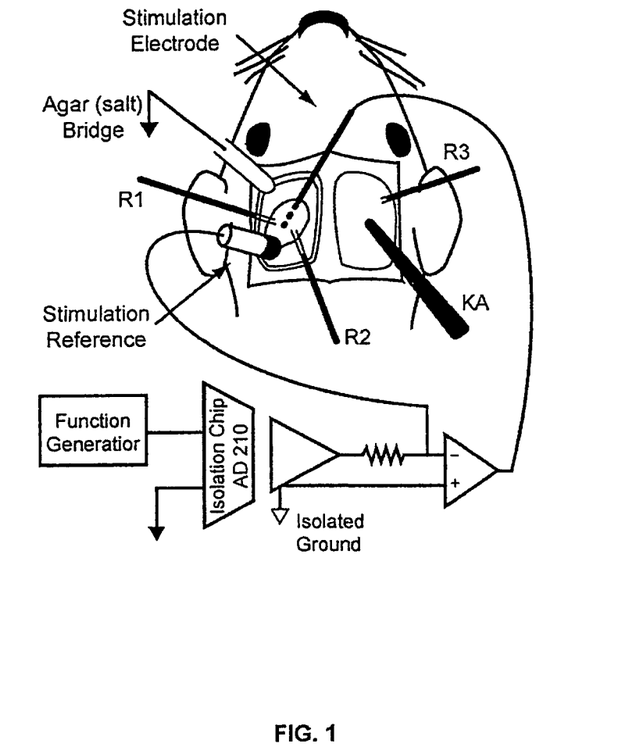
FIG. 1 shows a schematic of experimental preparation and stimulation electronics. R1, R2 and R3 are recording microelectrodes.

FIG. 1 shows a left hippocampus and hardware during experiment 4, and schematic of experimental preparation and stimulation electronics. Two recording microelectrode pairs (R1 and R2) may be inserted into the body of the exposed left hippocampus. A third recording microelectrode pair (R3) may be inserted through the intact right neocortex into the right hippocampus. An agar bridge placed in contact with the ACSF fluid layer over the rostral portion of the left cortical cavity served as measurement ground. An injection cannula (KA) for the perfusion of kainic acid into the right hippocampus may be inserted vertically into the CA1 through a dural window. The stimulation electrode may be inserted along the center axis of the exposed left hippocampus while the stimulation reference plate may be placed in the ACSF fluid layer in the lateral posterior region of the left neocortical window. The stimulation current may be created by a voltage-to-current amplifier with transformer-coupled isolation of both input and power (using an Analog Devices AD210) programmed from a standard waveform generator.

Differential microelectrode pairs (e.g., tungsten, 3 MΩ impedance, fixed 240 μm spacing, Frederic Haer Corporation) may be used for field potential recordings. Two electrode pairs may be inserted into the body of the left hippocampus to a depth of ~0.2 mm. Afterwards, a third recording electrode may be stereotactically inserted through the right neocortex into the body of the right hippocampus. Placing an additional agar bridge electrode in contact with the ACSF fluid layer in the left cortical window may serve as measurement ground. A schematic of electrode placements are shown in FIG. 1. Signals from the microelectrode pairs may be differentially preamplified with custom-built headstages (gain 10), and then conditioned using a standard amplifier bank (EX4-400, Dagan Corporation) with additional gains of 20-100 and bandpass filtered with high-pass frequency of 3-5 Hz and low-pass of 3 kHz. Each signal may then be digitally recorded using Axon Instruments hardware and software (12 bits/sample, 5 kHz; DigiData 1200a, Axoscope).

Closely spaced electrode pairs may be used to record field potentials differentially in order to minimize the effect of the applied electric field. The custom differential preamplifiers (based on instrumentation amplifiers Analog Devices AMP02 or Texas Instrument INA116) may accommodate common-mode signals between the recording electrodes and measurement ground produced by the applied electric field.

Stimulation Electrodes and Electronics.

Figure 2:
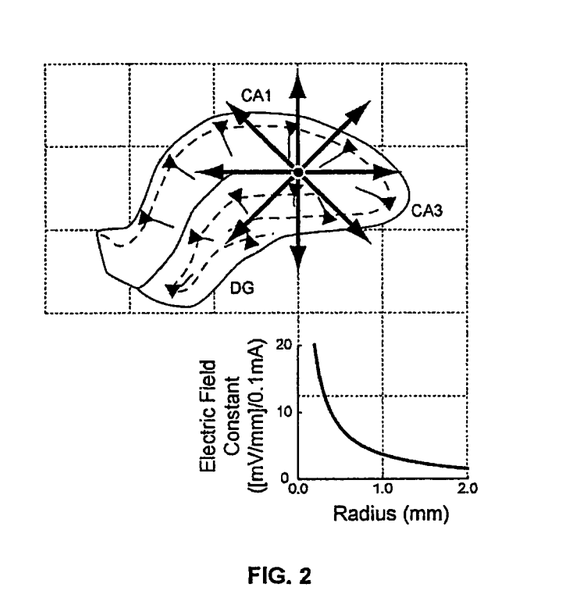
FIG. 2 shows an electric field geometry and amplitude for depth electrode placed axially within a hippocampus.

FIG. 2 shows an electric field geometry and amplitude for depth electrode placed axially within a hippocampus. For fixed stimulation electrodes, the electric field geometry is constant, while the amplitude of the field will be linearly proportional to the current applied between stimulation electrodes. The top illustrates the electric field geometry within perpendicular midplane of electrode from analytic calculation. The field is radial, and parallel to the long dendrite-soma axis of the pyramidal neurons in large regions of both CA3 and CA1. The bottom shows the proportionality constant between field and applied current, based on depth electrodes used (0.25 mm diameter, 5 mm long) and uniform tissue conductivity of 125 Ωcm. Along the perpendicular midplane, the field should fall off proportional to $$\frac{1}{rl\sqrt{1+4(r/l)^2}}$$

(solution for a finite length line source), where r is the radius and l is the length of the electrode.

A large-scale electric field may be applied by driving current between two electrodes in electrical contact with the tissue. A rod shaped depth electrode (Ag—AgCl, 0.25 mm diameter) may be inserted along the central axis of the left hippocampus to a depth of ~3 mm and referenced to a circular plate electrode (2-mm diameter Ag—AgCl) placed in the ACSF layer near the left hippocampus within the cortical window. The electric field from such an axially placed cylindrical electrode may be approximately radial, may fall off inversely proportional to the distance from the long axis, and may modulate large regions of CA3, CA2, and CA1 pyramidal neurons. An analytic approximation of the field, based on a uniform tissue conductivity of 125 Ωcm, is illustrated in FIG. 2.

A voltage-to-current amplifier with transformer-coupled isolation of both input and power (e.g., using an Analog Devices AD210) may create the stimulation current. This allows the stimulation electrode potentials to float with respect the measurement "ground." A waveform generator (e.g., Hewlett Packard 33120A) may be used to produce control signals.

Experimental Protocol

Overview.

A 0.25 mm (o.d.) cannula for the injection of kainic acid (KA) (e.g., OPIKA-1™ Kainic Acid, Ocean Produce International) may be inserted stereotactically into the right hippocampal CA1 (e.g., 5.6 mm posterior to bregma, 4.5 mm lateral, and 3.0 mm deep to the cortical surface) through the dural window and intact cortex. A microperfusion pump may be used to introduce 0.55 µl of 200 µg/µl KA into the hippocampus and may be repeated if needed at 20 min intervals (e.g., at one to six applications) until epileptiform activity may be observed. In an experiment, placing the KA loaded cannula into the CA1 may be sufficient to provoke epileptiform activity without administering bolus injections. Following such an experiment, animals may be euthanized with an overdose of anesthesia (e.g., 0.4-0.6 ml KX).

Electric Field Stimulation.

Figure 3:
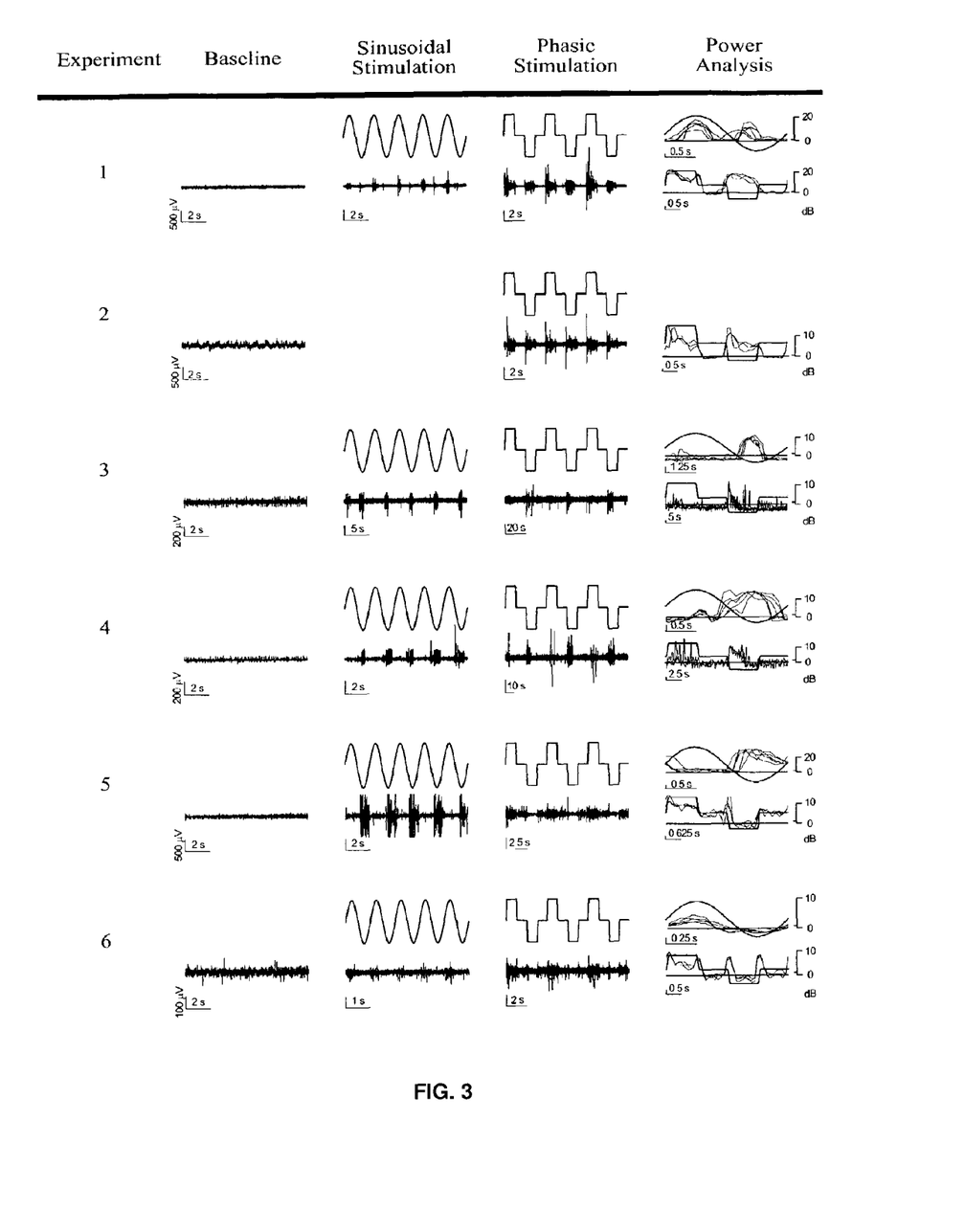
FIG. 3 illustrates a modulation of hippocampal field potential activity by sinusoidal and phasic radial electric field stimulation from six experiments.

FIG. 3 illustrates a modulation of hippocampal field potential activity by sinusoidal and phasic radial electric field stimulation from six experiments. Field potential traces may be measured from the stimulated hippocampus during baseline activity and during sinusoidal and multiphasic electrical stimulation. Calibration bars may be used to indicate field potential amplitude in mV (vertical) and time in seconds (horizontal). Amplitude and frequency of the stimuli and measurement electrode identification are listed in Table 1. The sinusoidally stimulated response trace from experiment 5 may be vertically clipped for presentation. Sinusoidal and phasic response data may be bandpass filtered (10-20 Hz to 2 kHz) to reduce stimulation artifact. In analyzing power, power may be calculated from 200 ms half-overlapped windows with phase of stimuli overlain, and plotted in decibels (dB) relative to average baseline power (dB=20 log(RAM/$RMS_{baseline}$)) for each period of stimulus shown in the traces. One standard deviation of window-to-window baseline power fluctuation may be indicated by left-heading hashmark (–) along vertical axes and may be used as an estimate of significance for observed fluctuations. One period of the stimulus may be overlaid as a visual guide.

Electric field stimulation may be applied with either sinusoidal or multi-phase square-waves (phasic) with varying amplitudes and periods. The phasic waveform may be constructed with consecutive plateaus of amplitude [0,1,0,–1] each of equal duration (see FIG. 3) and connected smoothly to minimize frequency components above 25 times the waveform frequency. Afterwards, other continuous waveforms, notably long DC pulses, may also be applied for exploratory purposes.

Analysis

Averages values may be presented as mean±standard deviation.

Peri-Stimulus RMS.

To remove residual stimulus artifact, recordings (e.g., baseline and during stimulation) may be digitally bandpass filtered with a second order Chebyshev filter (high-pass 10-20 Hz, low-pass 2 kHz). The degree of modulation may be quantified with the root mean squared (RMS) power in the pass band from the field potential recordings. The average RMS may be calculated in half overlapping 200 ms windows.

RMS Per Phase.

For the phasic stimuli, the RMS activity, a, may be calculated for each phase of the stimulus for measurements in both the stimulated and the KA hippocampus (e.g., electrodes R1 and R3 respectively). To further quantify the modulation of activity by the electric field as the ongoing activity changes, the normalized RMS deviation $\Delta=(\sigma-\bar{\sigma}_z)/\bar{\sigma}_z$, may be calculated, where $\sigma$ is the RMS activity averaged over either the positive or the negative phase of the stimulus, and $\bar{\sigma}_z$ is the RMS activity averaged over the previous and subsequent zero-amplitude phases of the stimulus.

Seizure Onset Times.

Seizure onset times may be defined when $\sigma$ for all stimulation phases on the KA side (electrode R3) exceeded threshold for 2 seconds. The threshold may be chosen at a convenient value that eliminated false positives. It may be possible to define a preseizure onset time when $\sigma$ exceeded the same threshold for just one phase of the phasic waveform over at least 2 waveform periods.

Results

Interictal Modulation

Electrical field modulation of ongoing hippocampal activity from the stimulated hippocampus is illustrated in FIG. 3. Shown are examples of the different stimuli and typical responses for each of the six experiments. Baseline traces represent activity in each experiment either immediately preceding or following electrical field application. Stimuli characteristics and recording electrode identification for this figure are summarized in Table 1.

Peristimulus RMS activity for each period of sinusoidal or phasic stimulus in the traces is shown in the power analysis. Vertical axes at the right are RMS power in dB referenced to the average RMS power calculated in 200 ms windows from 10 s of baseline data recorded near in time to each stimulation protocol. The standard deviation (STD) of the average baseline RMS $STD_{baseline}$ power is marked with a left-heading hash mark (–) on the power axes, and may be used as guide to estimate significance of the variations observed during stimulation. In each case, the maximum per period variation observed during stimulation is many times the baseline STD. This normalized deviation $(RMS_{max}-RMS_{baseline})/STD_{baseline}$, averaged over experiments, is 60±14 for sinusoidal and 136±55 for phasic stimuli.

In 5/6 experiments RMS analysis may reveal significant increase of activity at the positive and/or negative phase of the sinusoidal field. The neural response to particular phases of stimulation may vary between experiments. For example, in experiment 1 (row 1, FIG. 3) an increase in activity and RMS at both the positive and negative phases of the sinusoid may be observed. However, results may be indeterminate, as in experiment 2, where stimulus artifact may not be successfully removed from the recordings. As for experiments 3-6, excitation of the ongoing neural activity may occur at a single phase of the stimulation.

Similar results may be seen for the phasic stimulation. Excitation may occur at both the positive and negative phases of stimulation in experiments 1, 2 and 4. Experiment 3 may demonstrate excitation almost exclusively on the negative phase of stimulation. The last two experiments, 5 and 6, may demonstrate both excitation on the positive phase of stimulation and suppression of activity on the negative phase of the stimulation. This may be quantified below for a longer period from experiment 5 (FIGS. 4-7).

Figure 4:
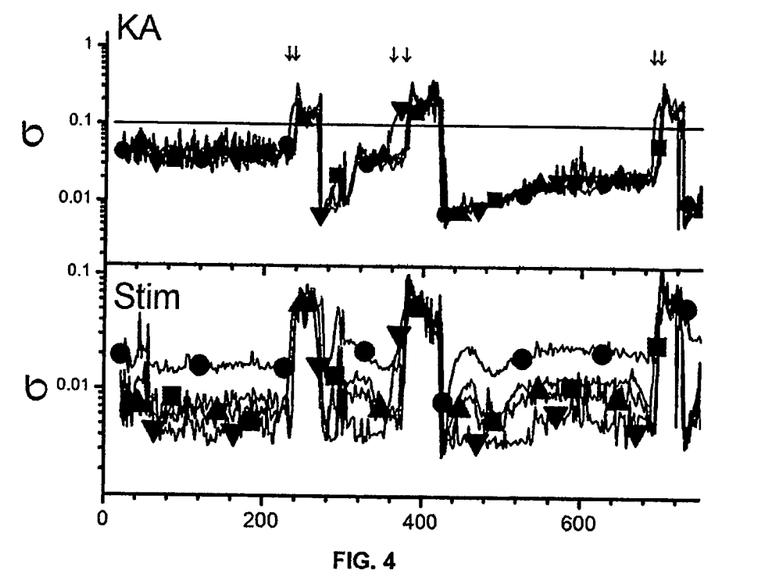
FIGS. 4-7 generally indicate bilateral modulation between and during seizures.

FIGS. 4-7 generally indicate bilateral modulation between and during seizures. (Experiment 5: phasic stimulus, 2 Hz period, amplitudes: 0.29 mA 0<t<225 s, 0.33 mA 225<t<685 s, 0.50 mA 685<t<1500 s). In each panel, the lower graphs correspond to measurements or analysis from the stimulated left hippocampus (Stim), and the upper graphs correspond to the right hippocampus that received the KA injection (KA). FIG. 4 specifically shows RMS Activity Per Phase, $\sigma$, during a 25 minute recording. Phase is coded ([1,0,–1,0]). Interictally, $\sigma$ for the stimulated hippocampus (lower graph) is typically higher during the positive phase of the stimulus and lowest during the negative phase. This pattern is violated during seizures.

Figure 5:
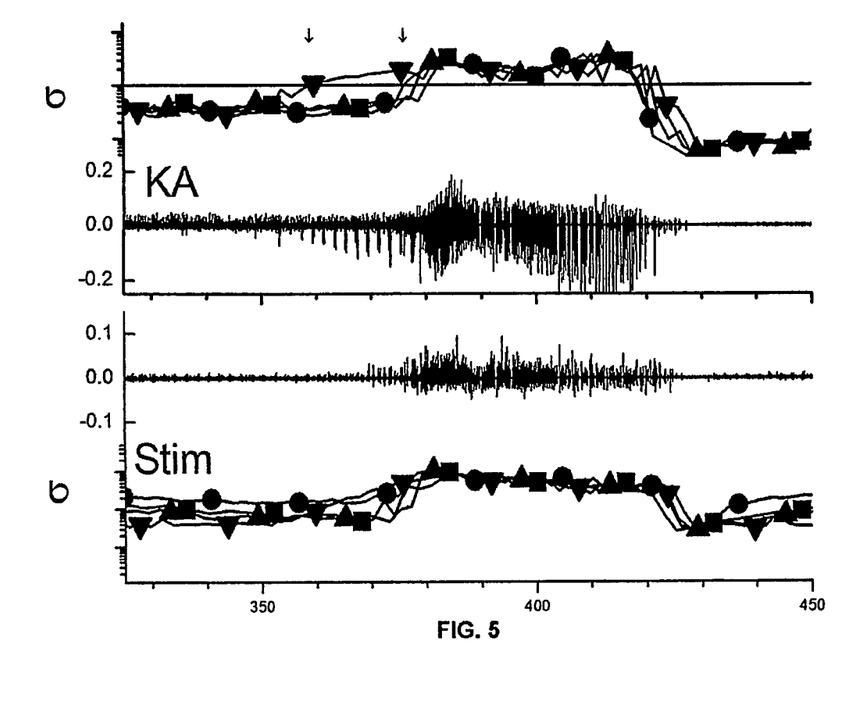

FIG. 5 specifically shows field potential traces and σ through the seizure at t=375 s. Vertical tick marks on traces correspond to 2 mV field potential deflections. Significant excitatory responses on the KA side (upper graphs) may be observed during the negative phase of the stimulus prior to the beginning of the seizure.

Figure 6:
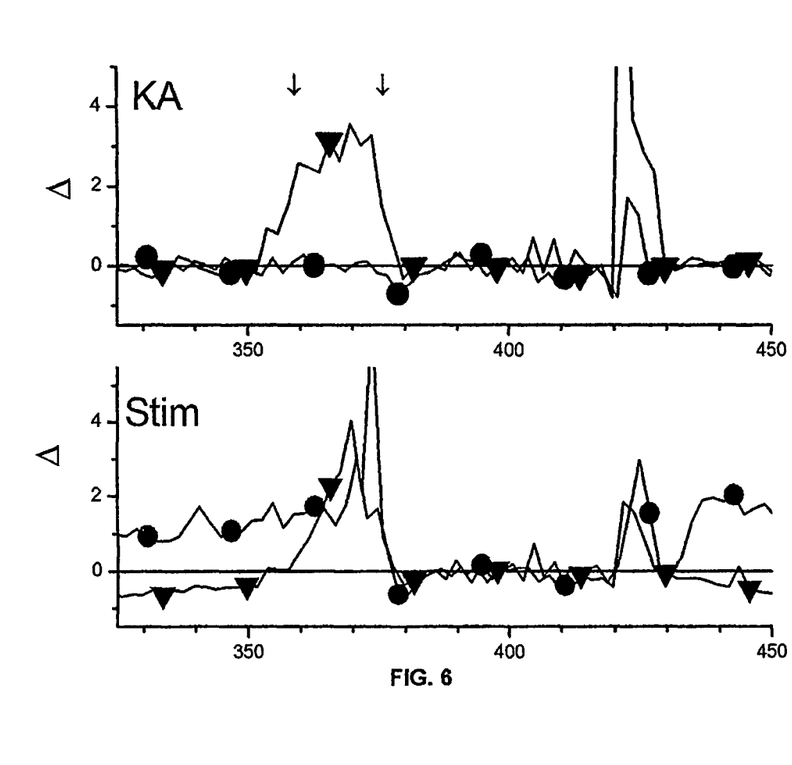

FIG. 6 specifically shows Normalized RMS deviation $\Delta=(\sigma-\bar{\sigma}_z)/\bar{\sigma}_z$, during the positive and negative phases of the stimulus for the same period as in FIG. 5. Contralateral to the stimulus (KA side), this measure increased dramatically prior to the seizure.

Figure 7:
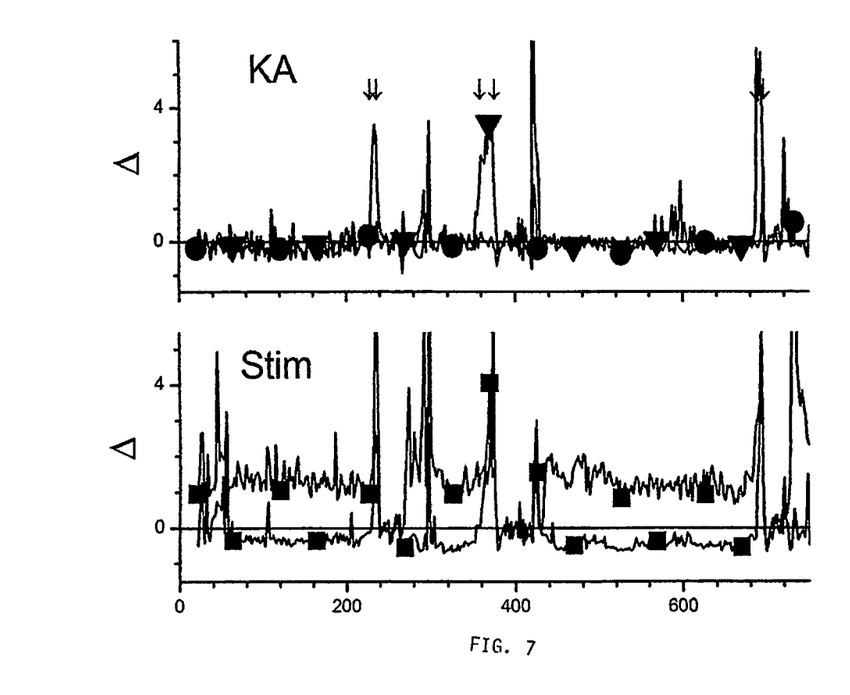

FIG. 7 specifically shows Δ for the same period as in FIG. 4. Contralateral to the stimulus (KA side), Δ increased for the negative phase at the beginning of each seizure. Seizure onset times defined when σ exceeded the threshold for all stimulus phases on KA side for at least 2 seconds. Preseizure onset times defined when σ exceeded the threshold for two consecutive stimuli periods only during the negative stimulus phase. Preseizure onset times precede seizure onset times by 14±2 s for the seven seizures observed.

Modulation Prior to Seizure Onset

Characteristic changes in the neuronal response to stimulation in advance of the electrographic seizures may be observed in two experiments (e.g., 1 and 5).

An example from experiment 5 of bilateral activity modulation may be shown in FIGS. 4-7 for 25 minutes of phasic electric field stimulation (e.g., period 2 s, amplitudes 0.29, 0.33 and 0.50 mA). The RMS activity per phase, σ, may be calculated for each 0.5 s phase of the stimulus for measurements in both the stimulated and the KA hippocampus (electrodes R1 and R3 respectively). Plotted in FIG. 4 is σ for recordings in each hippocampus. Ipsilateral to the stimulation (Stim, lower graph), the positive phase yielded higher σ than either zero phase, each of which may be higher than the negative phase. This pattern may be intermittently interrupted by periods with increased RMS that correspond to seizures. Electrographic seizure onsets times are defined as times when σ exceeded a threshold for 2 seconds (4 consecutive phases).

A bilateral recording of a single seizure is shown in FIG. 5. Many seconds in advance of seizure onset time, bursts of activity may be observed contralateral to the stimulus starting ~350 s (upper trace). These bursts typically occur only on the negative phase of the stimulus, when the stimulated hippocampus is suppressed. Preseizure times are defined as times when the activity on the KA side exceeded the same threshold as before for two consecutive stimulus periods but only during the negative phase of the stimulus. This preseizure onset time may precede the full onset time by 17 s in this example.

The normalized RMS deviation $\Delta=(\sigma-\bar{\sigma}_z)/\bar{\sigma}_z$, where a is the RMS activity averaged over either the positive or negative phase of the stimulus, and $\bar{\sigma}$, is the RMS activity averaged over the previous and subsequent zero-amplitude phases of the stimulus, may be introduced to further quantify the modulation of activity by the electric field as the ongoing activity changes. Excitatory modulation appears as a positive Δ and suppressive modulation as negative Δ. The normalized RMS deviation is shown in FIG. 6 for the same data as FIG. 5. On the KA side, the negative phases yield a positive Δ just before the seizure onsets. This increase in activity on the KA side was repeated prior to each of the seven seizures observed in the 25 minutes of recording, shown in FIG. 7. Preseizure onset times as defined above may precede full seizure onset times by 14±2 s averaged over the seven seizures observed in the 25 minutes of this recording.

TABLES

The following table shows characteristics for traces and stimuli presented in FIG. 3. Traces presented may be measured using electrodes R1 or R2 as shown in FIG. 2. Amplitudes are peak-zero.

TABLE 1

| | | Sinusoidal | | Phasic Stimulation | |
|---|---|---|---|---|---|
| Experiment | Recording Electrode | Amplitude (mA) | Frequency (Hz) | Amplitude (mA) | Frequency (Hz) |
| 1 | R2 | 0.25 | 0.5 | 1.0 | 0.25 |
| 2 | R1 | | | 0.1 | 0.25 |
| 3 | R2 | 1.25 | 0.2 | 1.2 | 0.025 |
| 4 | R2 | 1.0 | 0.5 | 1.2 | 0.05 |
| 5 | R1 | 0.37 | 0.5 | 0.3 | 0.2 |
| 6 | R1 | 0.05 | 1.0 | 0.01 | 0.25 |

Table 2 shows charge passage statistics for each experiment calculated. Unbalanced Charge, $$Q_{unbal}(T) = \int_{T_0}^{T} I(t)dt,$$

may be computed by integrating the applied current. Maximum Unbalanced Charge may be computed as the largest absolute value $Q_{unbal}$ during one stimulus period or full experiment. Unbalanced Charge at end of experiment may be computed from beginning to end of experiment. For most experiments, the periodic waveforms may apply relatively low maximal charge variations. The majority of unbalanced charge came from non-periodic stimuli applied after the experiments reported here. Total Charge Passed may be computed by integrated absolute value of current, $$Q_{pass}(T) = \int_{T_0}^{T} |I(t)|dt.$$

The severe lesioning observed in experiment 3 may be attributed to the maximum unbalanced charge passed, and not the total charge passed.

TABLE 2

| Experiment | Maximum Unbalanced Charge $Q_{unbal}$ per cycle of periodic stimulus (mC) | Maximum Unbalanced Charge $Q_{unbal}$ during experiment (mC) | Unbalanced Charge $Q_{unbal}$ at end of experiment (mC) | Total Charge Passed $Q_{pass}$ (mC) |
|---|---|---|---|---|
| 1 | 1.0 | 9.7 | −1.0 | 105 |
| 2 | 0.16 | 3.9 | −3.9 | 105 |
| 3 | 15.0 | 57.5 | −52.9 | 835 |
| 4 | 6.0 | 6.0 | 0.0 | 421 |
| 5 | 1.55 | 9.6 | 1.5 | 624 |
| 6 | 0.05 | 4.6 | −2.9 | 32 |

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever. The entire disclosure of all patents and publications, cited above and in the figures are hereby incorporated in their entirety by reference, including U.S. Provisional Application Ser. No. 60/422,870, filed, Nov. 1, 2002.

From the foregoing description, one skilled in the art can easily ascertain the essential characteristics of this invention, and without departing from the spirit and scope thereof, can make various changes and modifications of the invention to adapt it to various usages and conditions. For example, even though the present description describes embodiments of the present invention where sensing measurements maybe made at around a singular location, it is envisioned that other embodiments will be capable of making and using multiple measurements from multiple localities (e.g., different parts of the hippocampus) when characterizing the state of a neural system.

We claim:

1. A method for detecting an impending seizure in a neural system, comprising:
    applying a subthreshold electrical stimulus which comprises low frequency content to a neural system,
    detecting a first response of the neural system to said subthreshold electrical stimulus during an interictal state and a second response of the neural system to said subthreshold electrical stimulus during a state indicative of an impending seizure, wherein said subthreshold electrical stimulus comprises an arbitrary waveform that is determined adaptively by the magnitude and frequency of a preceding or concurrent response, and
    determining whether said second response during the state indicative of an impending seizure is different from said first response during the interictal state, whereby an impending seizure is detected.

2. A method of claim 1, wherein the stimulus is characterized by voltage, current, or field strength.

3. A method of claim 1, wherein the stimulus is less than 1000 mV/mm.

4. A method of claim 1, wherein the stimulus is oriented parallel to the somatic-dendritic axis of the neurons in the neural system.

5. A method of claim 1, wherein the stimulus is an electrical field produced using two field electrodes positional external to the neurons in the neural system.

6. A method of claim 1, wherein a plurality of stimuli are applied and the interval between each stimulus is more than 1 second.

7. A method of claim 1, wherein the detecting the response is measuring neuronal activity of the neural system.

8. A method of claim 7, wherein the measuring of the neuronal activity is performed simultaneously and continuously with the applied stimulus.

9. A method of claim 7, wherein the neuronal activity is characterized by root-mean-square.

10. A method of claim 1, wherein the frequency and amplitude of the applied stimulus is insufficient to evoke action potentials in the neurons that comprise said neural system.

11. A method of claim 1, further comprising, when a impending or preseizure state is detected,
    applying an oriented electric field or current to said neural system effective to suppress the seizure activity of the neural system, wherein the magnitude and polarity of said oriented electric field is changed in response to the measured neuronal activity, and the measuring of neuronal activity is performed simultaneously and continuously with the applied field.

12. The method according to claim 1, wherein said subthreshold electrical stimulus is an electrical stimulus which is less than 100 V/mm.

13. The method according to claim 1, wherein said subthreshold electrical stimulus is an electrical stimulus which is less than 10 V/mm.

14. The method according to claim 1, wherein said subthreshold electrical stimulus is less than or equal to 100 Hz.

15. The method according to claim 1, wherein said subthreshold electrical stimulus is a low frequency content.

16. The method according to claim 1, comprising
    detecting a first response of the neural system to said subthreshold electrical stimulus during an interictal state and a second response of the neural system to said subthreshold electrical stimulus during an unresolved state, wherein said subthreshold electrical stimulus comprises an arbitrary waveform that is determined adaptively by the magnitude and frequency of a preceding or a concurrent response; and
    determining whether said second response during the unresolved state is different from said first response during the interictal state, whereby an impending seizure is detected.

17. A method for detecting an impending seizure in a neural system, comprising:
    applying a subthreshold electrical stimulus to a neural system,
    detecting a first response of the neural system to said subthreshold electrical stimulus during an interictal state and a second response of the neural system to said subthreshold electrical stimulus during a state indicative of an impending seizure, wherein said electrical stimulus comprises an arbitrary waveform that is determined adaptively by the magnitude and frequency of a preceding or concurrent response, and
    determining whether said second response during the state indicative of an impending seizure is different from said first response during the interictal state, whereby an impending seizure is detected.

18. The method according to claim 17, wherein said subthreshold electrical stimulus is less than or equal to 100 Hz.

19. A method for detecting an impending seizure in a neural system, comprising:
    applying a subthreshold electrical stimulus which comprises a continuous waveform to a neural system,
    detecting a first response of the neural system to said subthreshold electrical stimulus during an interictal state and a second response of the neural system to said subthreshold electrical stimulus during a state indicative of an impending seizure, wherein said electrical stimulus comprises an arbitrary waveform that is determined adaptively by the magnitude and frequency of a preceding response, and
    determining whether said second response during the state indicative of an impending seizure is different from said first response during the interictal state, whereby an impending seizure is detected.

20. The method according to claim 19, wherein said subthreshold electrical stimulus is less than or equal to 100 Hz.

21. A method for detecting an impending seizure in a neural system, comprising:
    applying a subthreshold electrical stimulus to a neural system, wherein said subthreshold electrical stimulus comprises an arbitrary waveform that is determined adaptively by the magnitude and frequency of a preceding or concurrent response,
    detecting a first response of the neural system to said subthreshold electrical stimulus during an interictal state and a second response of the neural system to said subthreshold electrical stimulus during a state indicative of an impending seizure, and determining whether said second response during the state indicative of an impending seizure is different from said first response during the interictal state, whereby an impending seizure is detected.

22. A method of claim 21, wherein said electrical stimulus consists of low frequency content.

23. A method of claim 21, wherein said electrical stimulus is a continuous waveform.

* * * * *